US012636120B2

(12) United States Patent
Zehavi et al.

(10) Patent No.: US 12,636,120 B2
(45) Date of Patent: May 26, 2026

(54) SYSTEMS, METHODS, AND DEVICES FOR DETERMINING AN OBJECT POSE

(71) Applicant: Mazor Robotics Ltd., Caesarea (IL)

(72) Inventors: Eli Zehavi, Tel Aviv (IL); Yonatan Ushpizin, Glil Yam (IL); Ido Zucker, Tel Aviv (IL); Adi Ess, Ramat Gan (IL)

(73) Assignee: Mazor Robotics Ltd., Caesarea (IL)

( * ) Notice: Subject to any disclaimer, the term of this patent is extended or adjusted under 35 U.S.C. 154(b) by 253 days.

(21) Appl. No.: 18/559,348

(22) PCT Filed: May 23, 2022

(86) PCT No.: PCT/IL2022/050538
§ 371 (c)(1),
(2) Date: Nov. 7, 2023

(87) PCT Pub. No.: WO2022/249168
PCT Pub. Date: Dec. 1, 2022

(65) Prior Publication Data
US 2024/0225752 A1      Jul. 11, 2024

Related U.S. Application Data

(60) Provisional application No. 63/193,928, filed on May 27, 2021.

(51) Int. Cl.
*A61B 90/00*      (2016.01)
*A61B 34/20*      (2016.01)
*A61B 34/37*      (2016.01)

(52) U.S. Cl.
CPC ...... *A61B 90/39* (2016.02); *A61B 2034/2055* (2016.02); *A61B 34/37* (2016.02);
(Continued)

(58) Field of Classification Search
CPC ..... A61B 2034/2055–2057; A61B 2090/3937; A61B 2090/3945; A61B 2090/3975; A61B 2090/3979
See application file for complete search history.

(56) References Cited

U.S. PATENT DOCUMENTS 5,828,770 A * 10/1998 Leis ..................... C12Q 1/6806
382/103
10,816,632 B1 10/2020 Menon et al.
(Continued)

FOREIGN PATENT DOCUMENTS

WO      WO 2020/264489 A1      12/2020
WO      WO 2021/059253 A2      4/2021

OTHER PUBLICATIONS

International Search Report for PCT/IL2022/050538 date of completion is Sep. 16, 2022 (5 pages).

*Primary Examiner* — Angela M Hoffa
(74) *Attorney, Agent, or Firm* — Sheridan Ross P.C.

(57) ABSTRACT

Systems, methods, and devices for determining a tool pose are provided. A tracking device mounted to a tool may comprise a plurality of faces and a plurality of markers defining a plurality of sets of markers. Each set of markers may comprise one or more markers of the plurality of markers and each set of markers may be disposed on a corresponding face. Information about a set of markers of the plurality of markers may be received. A face of the plurality of faces having the set of markers disposed thereon may be determined. A pose of the tool based on the information and the determined face may be determined.

14 Claims, 9 Drawing Sheets

500

504 — Cause a controller to activate one marker from a set of markers

508 — Receive information about a detected activated marker

512 — Cause the controller to activate the set of markers comprising the detected activated marker 516 — Receive information about the activated set of markers 520 — Determine a face of a plurality of faces having the activated set of markers 524 — Determine a pose of a tool and/or a robotic arm based on the information and the determined face 528 — Validate a pose of the tool and/or the robotic arm

(52) U.S. Cl.
CPC ................. *A61B 2090/3937* (2016.02); *A61B 2090/3945* (2016.02); *A61B 2090/3979* (2016.02)

(56) References Cited

U.S. PATENT DOCUMENTS

| | | | | |
|---|---|---|---|---|
| 11,612,440 | B2 * | 3/2023 | Coakley ................ | A61B 90/39 |
| | | | | 348/77 |
| 12,064,190 | B2 * | 8/2024 | Ghanam ................ | A61B 34/20 |
| 2008/0161682 | A1 | 7/2008 | Kendrick et al. | |
| 2018/0092699 | A1 | 4/2018 | Finley | |
| 2018/0325610 | A1 | 11/2018 | Cameron et al. | |
| 2020/0146754 | A1 | 5/2020 | Row et al. | |
| 2021/0068903 | A1 * | 3/2021 | Coakley ................ | A61B 90/39 |
| 2021/0236212 | A1 * | 8/2021 | Ghanam ................... | G06T 7/20 |
| 2022/0087773 | A1 * | 3/2022 | Herrmann ............. | A61B 90/39 |
| 2023/0248446 | A1 * | 8/2023 | Coakley ................ | A61B 34/20 |
| | | | | 348/77 |
| 2024/0268921 | A1 * | 8/2024 | Herrmann ............. | A61B 90/39 |
| 2025/0032193 | A1 * | 1/2025 | Termeer ................ | A61B 34/20 |
| 2025/0120785 | A1 * | 4/2025 | Halverson ............. | A61B 90/10 |

* cited by examiner

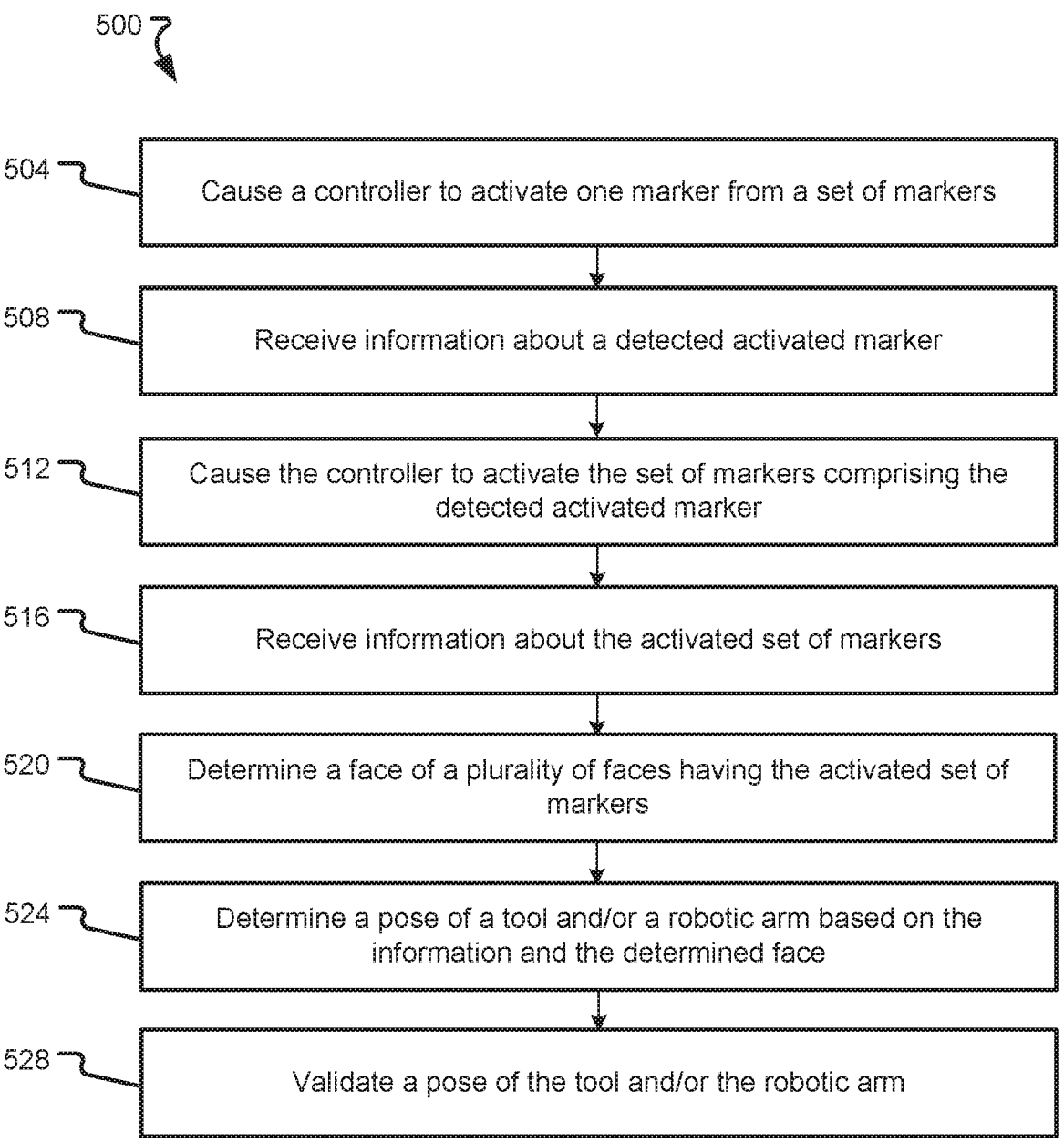

500

504 — Cause a controller to activate one marker from a set of markers

508 — Receive information about a detected activated marker

512 — Cause the controller to activate the set of markers comprising the detected activated marker 516 — Receive information about the activated set of markers 520 — Determine a face of a plurality of faces having the activated set of markers 524 — Determine a pose of a tool and/or a robotic arm based on the information and the determined face 528 — Validate a pose of the tool and/or the robotic arm

604 — Cause a controller to selectively activate one or more markers of a first tracking device and one or more markers of a second tracking device 608 — Cause the controller to activate the markers on the first tracking device in a first configuration 612 — Cause the controller to activate the markers on the second tracking device in a second configuration

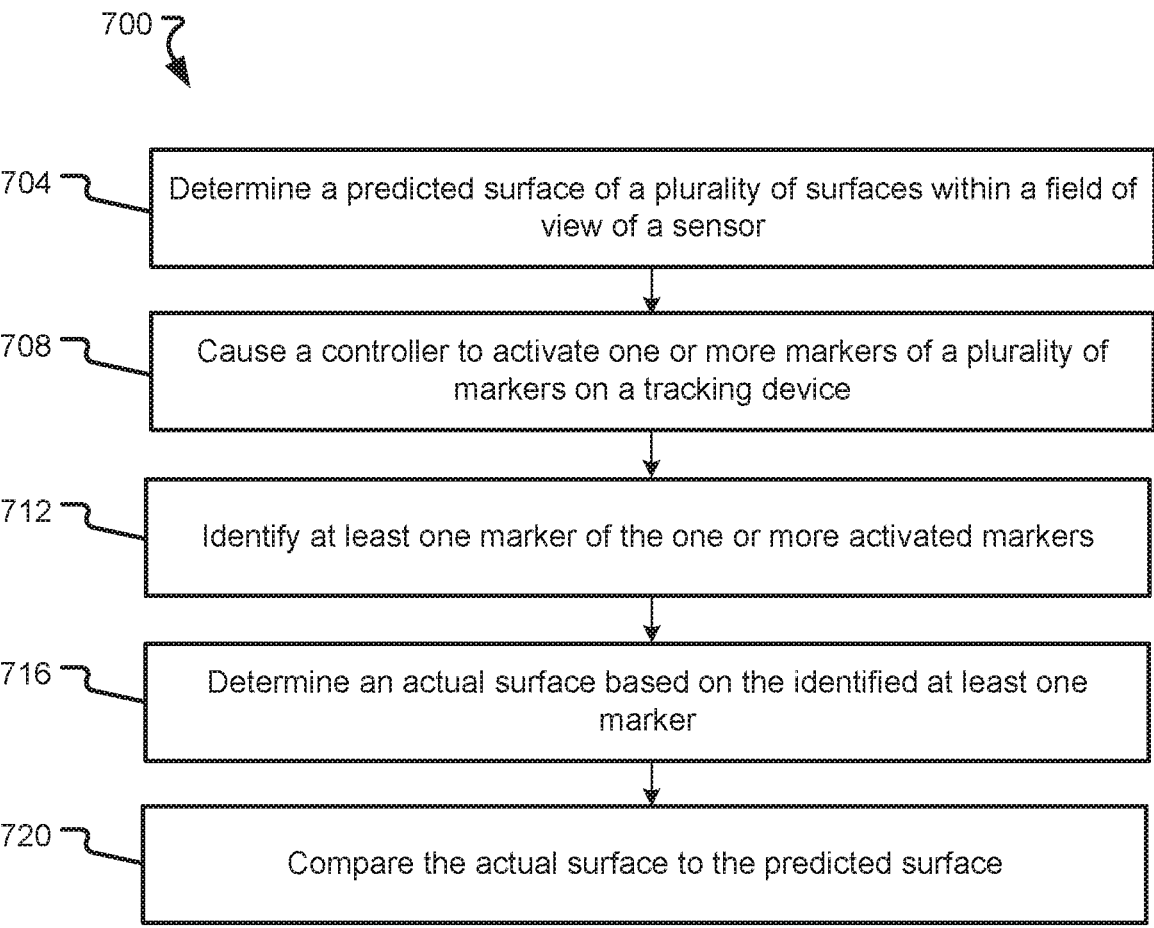

700

704 — Determine a predicted surface of a plurality of surfaces within a field of view of a sensor 708 — Cause a controller to activate one or more markers of a plurality of markers on a tracking device 712 — Identify at least one marker of the one or more activated markers 716 — Determine an actual surface based on the identified at least one marker 720 — Compare the actual surface to the predicted surface

FIG. 7

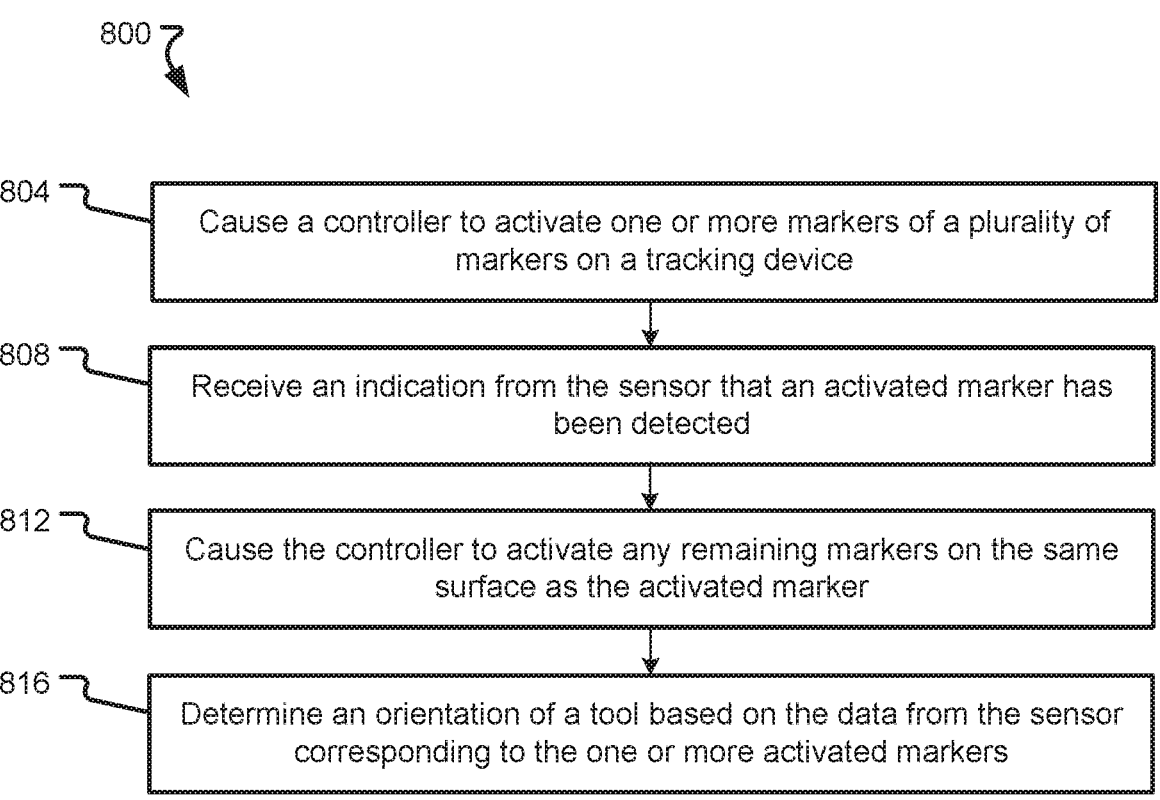

800

804 — Cause a controller to activate one or more markers of a plurality of markers on a tracking device 808 — Receive an indication from the sensor that an activated marker has been detected 812 — Cause the controller to activate any remaining markers on the same surface as the activated marker 816 — Determine an orientation of a tool based on the data from the sensor corresponding to the one or more activated markers

FIG. 8

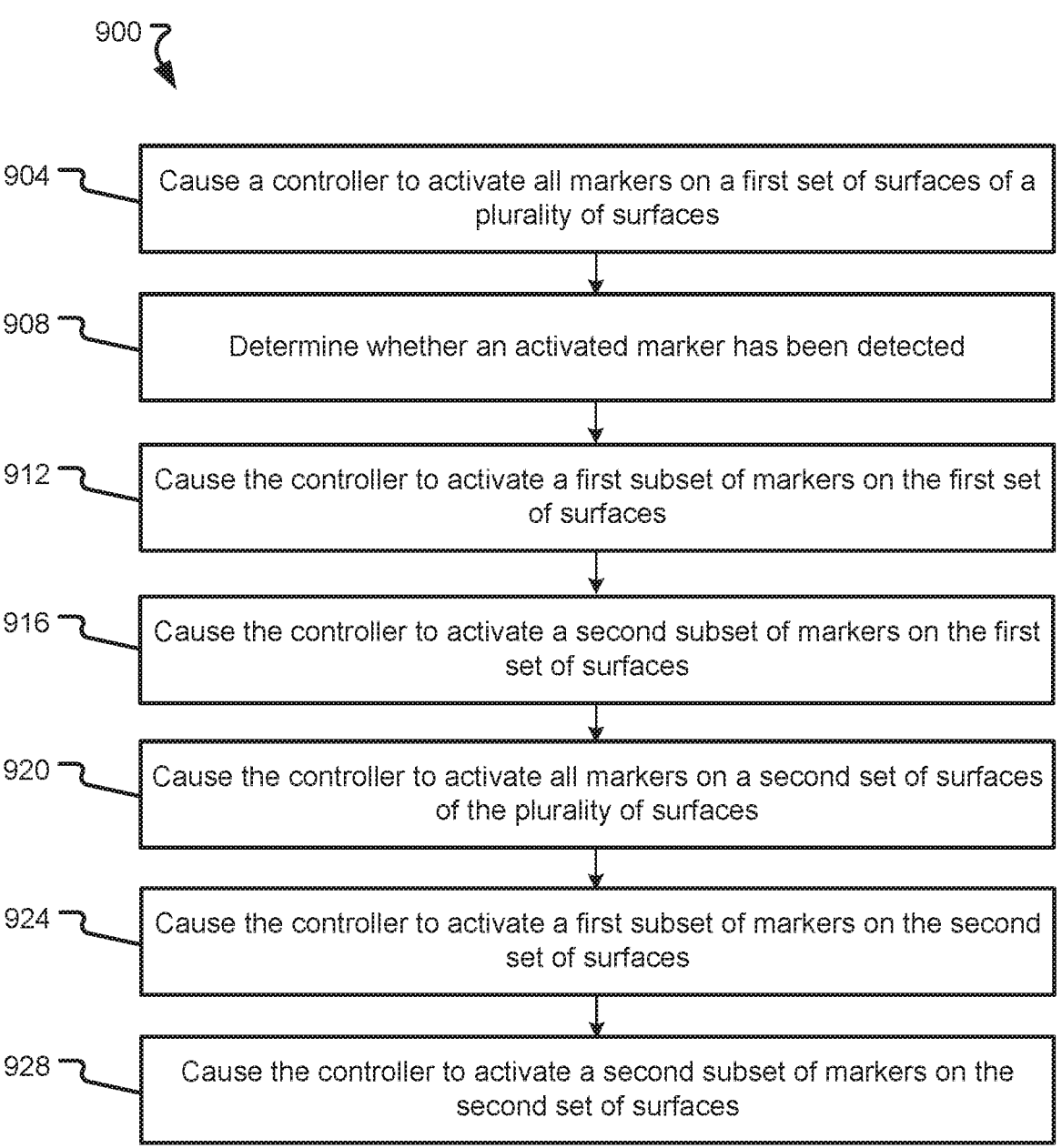

900

904 — Cause a controller to activate all markers on a first set of surfaces of a plurality of surfaces 908 — Determine whether an activated marker has been detected 912 — Cause the controller to activate a first subset of markers on the first set of surfaces 916 — Cause the controller to activate a second subset of markers on the first set of surfaces 920 — Cause the controller to activate all markers on a second set of surfaces of the plurality of surfaces 924 — Cause the controller to activate a first subset of markers on the second set of surfaces 928 — Cause the controller to activate a second subset of markers on the second set of surfaces

FIG. 9

SYSTEMS, METHODS, AND DEVICES FOR DETERMINING AN OBJECT POSE

CROSS-REFERENCE TO RELATED APPLICATIONS

This application is a National Stage Application of PCT/IL2022/050538 filed May 23, 2022, which claims benefit of and priority to U.S. Provisional Application No. 63/193,928 filed May 27, 2021, and the disclosures of each of the above-identified applications are hereby incorporated by reference in their entirety.

FIELD

The present technology generally relates to determining a pose of an object, and relates more particularly to mounting a tracking device on an object to determine a pose of the object.

BACKGROUND

Surgical robots may assist a surgeon or other medical provider in carrying out a surgical procedure, or may complete one or more surgical procedures autonomously. Reference markers on an object, or the object itself may be used by a medical provider to detect and/or track the object during the surgical procedure. The reference markers may be disposed on any object such as a robotic arm, an end effector, an instrument, or a tool.

SUMMARY

Example aspects of the present disclosure include:

A system for determining a tool pose according to at least one embodiment of the present disclosure comprises a tracking device mounted to a tool and comprises: a plurality of faces; a plurality of markers defining a plurality of sets of markers, each set of markers comprising one or more markers of the plurality of markers, each set of markers disposed on a corresponding face; at least one processor; and a memory storing data for processing by the at least one processor that, when processed, the data causes the at least one processor to: receive information about a set of markers of the plurality of markers, determine a face of the plurality of faces having the set of markers disposed thereon, and determine a pose of the tool based on the information and the determined face.

Any of the aspects herein, wherein the information includes a detected position of each marker of the set of markers.

Any of the aspects herein, wherein each adjacent set of markers share at least two markers.

Any of the aspects herein, wherein a first set of markers is arranged in a different pattern than a second set of markers.

Any of the aspects herein, wherein the information is received from a camera.

Any of the aspects herein, wherein the tool is supported by a robotic arm.

Any of the aspects herein, wherein the markers are infrared light emitting diodes.

Any of the aspects herein, wherein the markers are infrared light emitting diodes.

Any of the aspects herein, further comprising: a controller configured to selectively cause one or more markers of the set of markers to emit infrared light.

Any of the aspects herein, wherein the memory stores additional data for execution by the at least one processor that, when processed, further cause the at least one processor to: cause the controller to activate only one marker from each set of markers, in sequence; receive information about a detected activated marker; and cause the controller to activate the set of markers comprising the detected activated marker.

Any of the aspects herein, further comprising: a sensor configured to detect the set of markers, wherein the information is received from the sensor.

Any of the aspects herein, wherein the plurality of faces extend around a circumference of the tool.

A tracking device according to at least one embodiment of the present disclosure comprises a body; a first ring supported by the body; a second ring supported by the body, the second ring axially aligned with the first ring and spaced from the first ring; and a first plurality of markers disposed on the first ring and a second plurality of markers disposed on the second ring, the first plurality of markers and the second plurality of markers defining a plurality of sets of markers, each set of markers comprising one or more markers of each of the first plurality of markers and the second plurality of markers, each set of markers define a corresponding face of a plurality of faces.

Any of the aspects herein, wherein a first set of markers of the plurality of sets of markers is disposed in a first pattern and a second set of markers of the plurality of sets of markers is disposed in a second pattern.

Any of the aspects herein, wherein the second pattern is an inverse pattern of the first pattern.

Any of the aspects herein, wherein the first pattern and the second pattern are each a trapezoid.

Any of the aspects herein, wherein each set of markers includes at least three markers.

Any of the aspects herein, wherein the plurality of faces includes eight adjacent faces, each face adjacent to two other faces.

A system for tracking multiple objects according to at least one embodiment of the present disclosure comprises a first tracking device and a second tracking device, wherein the first tracking device and the second tracking device each comprise: a plurality of faces, and a plurality of markers defining a plurality of sets of markers, each set of markers comprising one or more markers of the plurality of markers, each set of markers disposed on a corresponding face, a controller configured to selectively activate one or more markers of the plurality of markers; at least one processor; and a memory storing data for processing by the at least one processor that, when processed, the data causes the at least one processor to: cause the controller to selectively activate one or more markers of the plurality of markers on the first tracking device and one or more markers of the plurality of markers on the second tracking device.

Any of the aspects herein, wherein each marker on the first tracking device has a first arrangement and each marker on the second tracking device has a second arrangement.

Any of the aspects herein, wherein the first arrangement different from the second arrangement.

Any of the aspects herein, wherein the second arrangement is identical to the first arrangement.

Any of the aspects herein, wherein the memory stores additional data for execution by the at least one processor that, when processed, further cause the at least one processor to: cause the controller to activate the markers on the first tracking device in a first sequence, and cause the controller to activate the markers on the second tracking device in a second sequence.

Any of the aspects herein, wherein the memory stores additional data for execution by the at least one processor that, when processed, further cause the at least one processor to: cause the controller to activate the markers on the first tracking device in a first wavelength, and cause the controller to activate the markers on the second tracking device in a second wavelength.

A system for determining a tool pose according to at least one embodiment of the present disclosure comprises a tracking device mounted to a tool and comprising: a plurality of segments, and a plurality of markers defining a plurality of sets of markers, each set of markers comprising one or more markers of the plurality of markers, each set of markers disposed on a corresponding segment, a controller configured to selectively activate one or more markers of the plurality of markers on each segment; a sensor having a field of view and configured to detect activated markers within the field of view; at least one processor; and a memory storing data for processing by the at least one processor that, when processed, the data causes the at least one processor to: cause the controller to selectively activate one or more markers of the plurality of markers on the tracking device; and determine an orientation of the tool based on data from the sensor corresponding to the one or more activated markers, the one or more activated markers disposed on a single segment of the plurality of segments, wherein markers not on the single segment are not activated.

Any of the aspects herein, wherein the tool is supported by a robotic arm.

Any of the aspects herein, wherein causing the controller to selectively activate one or more markers of the plurality of markers causes the controller to activate one or more markers on a predicted segment, and wherein the memory stores additional data for execution by the at least one processor that, when processed, further cause the at least one processor to: determine, based on a known pose of the robotic arm, the predicted segment of the plurality of segments within the field of view; identify, using the sensor, at least one marker of the one or more activated markers; determine an actual segment based on the identified at least one marker; and compare the actual segment to the predicted segment to confirm the actual segment matches the predicted segment.

Any of the aspects herein, wherein causing the controller to selectively activate one or more markers of the plurality of markers causes the controller to activate, in sequence, a single marker on each of the plurality of segments, and wherein the memory stores additional data for execution by the at least one processor that, when processed, further cause the at least one processor to: receive an indication from the sensor that an activated marker has been detected; and cause the controller to activate any remaining markers on the same segment as the activated marker.

A system for determining a tool pose according to at least one embodiment of the present disclosure comprises a tracking device mounted to a tool and comprising: a plurality of segments, and a plurality of markers defining a plurality of sets of markers, each set of markers comprising one or more markers of the plurality of markers, each set of markers disposed on each segment, a controller configured to selectively activate one or more markers of the plurality of markers on each segment; a sensor having a field of view and configured to detect activated markers within the field of view; at least one processor; and a memory storing data for processing by the at least one processor that, when processed, the data causes the at least one processor to: cause the controller to activate all of the markers on a first set of segments of the plurality of segments, and determine, based on data from the sensor, whether an activated marker has been detected; when an activated marker has been detected, cause the controller to activate a first subset of markers on the first set of segments of the plurality of segments; and when an activated marker has not been detected, cause the controller to activate all of the markers on a second set of segments of the plurality of segments, the first set and the second set of the plurality of segments comprising all of the plurality of segments.

Any of the aspects herein, wherein the memory stores additional data for execution by the at least one processor that, when processed, further cause the at least one processor to: when an activated marker of the first subset of markers on the first set of segments of the plurality of segments has not been detected, cause the controller to activate a second subset of markers on the first set of segments of the plurality of segments.

Any of the aspects herein, wherein the memory stores additional data for execution by the at least one processor that, when processed, further cause the at least one processor to: when an activated marker has been detected from markers on the second set of segments of the plurality of segments, cause the controller to activate a first subset of markers on the second set of segments of the plurality of segments.

Any of the aspects herein, wherein the memory stores additional data for execution by the at least one processor that, when processed, further cause the at least one processor to: when an activated marker of the first subset of markers on the second set of segments of the plurality of segments has not been detected, cause the controller to activate a second subset of markers on the second set of segments of the plurality of segments.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 5 is a flowchart according to at least one embodiment of the present disclosure;

FIG. 7 is a flowchart according to at least one embodiment of the present disclosure;

FIG. 8 is a flowchart according to at least one embodiment of the present disclosure; and FIG. 9 is a flowchart according to at least one embodiment of the present disclosure.

DETAILED DESCRIPTION

Figure 1:
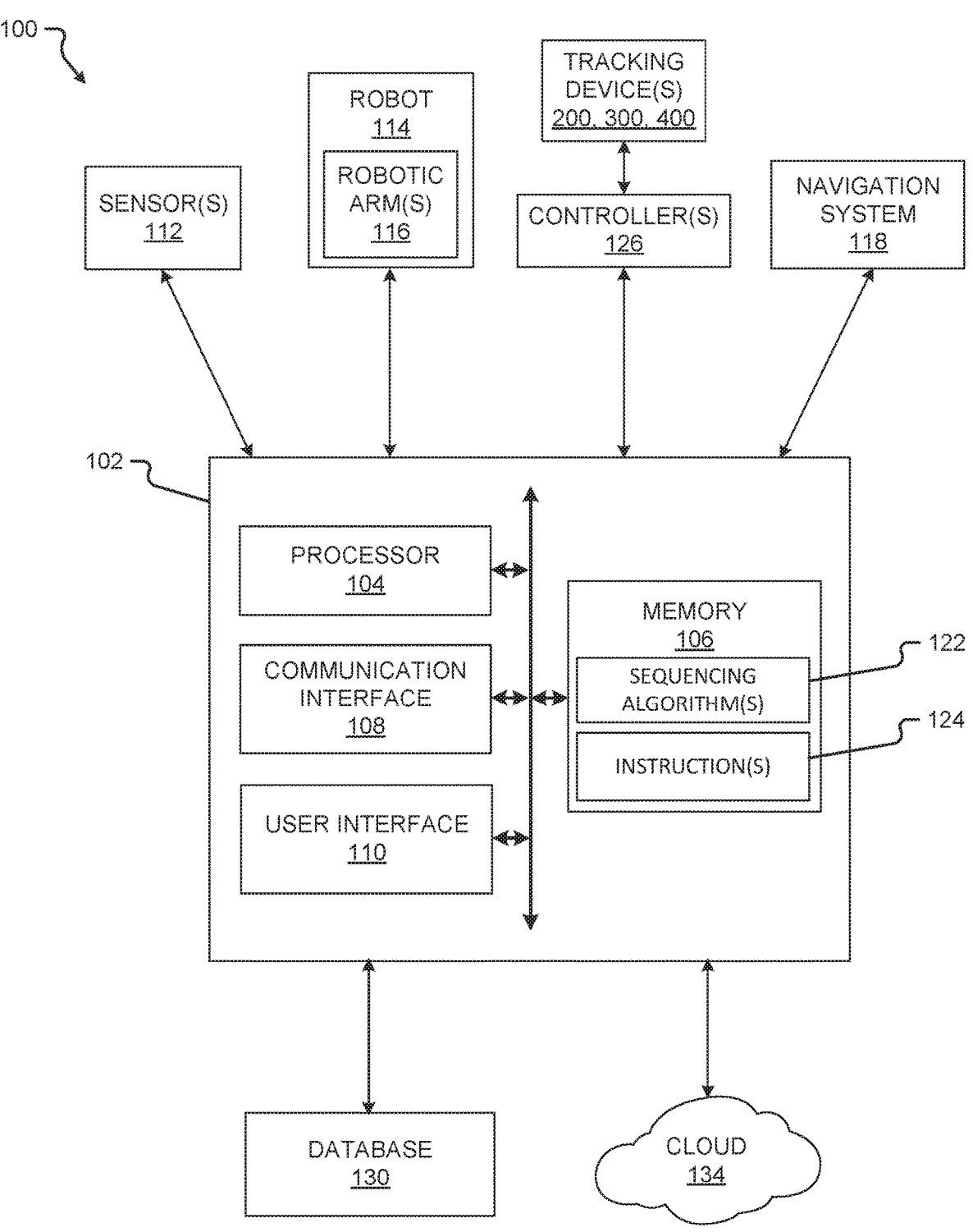
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Part of a robotic guided spine surgery may involve ascertaining a position or pose of a robot used for the spine surgery, though it will be appreciated that the position or pose of a robot may be ascertained in other types of surgical procedures. One suggested method to perform a desired validation of the robot position or pose uses, for example, optical tracking of active markers on a multi-faced tool. The active markers may include infrared light emitting diodes (IREDs) mounted on a ceramic base, for example. A position sensor (such as, for example, a camera or an infrared camera) may detect the infrared light emitted by activated markers. A system such as a navigation system or a computing system, for example, can report the positions of the markers individually, and can calculate a position and orientation of one or more tools that incorporate the markers.

One embodiment of a multi-faced tool may be a tool with markers arranged into faces of the tool. In some examples, the position sensor may track only one face at a time. In some instances, the markers on a multi-faced tool may not all be detected simultaneously by the position sensor. A multi-faced tool may be beneficial if an intended application requires the tool to rotate beyond a maximum marker angle. The integration of the active wired tool with the robotic arm may allow for continuous tracking of the position of the robotic arm and its orientation.

Active tools may be physically connected to the system such as, for example, the navigation system or a computing system, and incorporate the active markers. To track an active tool, the position sensor detects, for example, infrared light emitted by the active markers. The system may control the markers (to selectively emit, for example, infrared light) through a wired connection to a system control unit of the system. To identify the tool, the system control unit may trigger the IREDs or LEDs in synchronization (e.g., according to a predetermined pattern) until the system control unit finds enough IREDs or LEDs to calculate a tool's transformation. If the system control unit tries to track a unique geometry tool, the IREDs or LEDs may be sequenced all at the same time since the tool orientation can be detected by the unique shape.

For a multi-faced tool, in instances where the tool may go missing, the system control unit may illuminate one marker at a time until the marker is in view of the position sensor. The position sensor may then lock on the face that the marker is a part of (and may sequence each IRED or LED in the face to find an orientation of the face). To reduce a lock-on time it is possible to use a combination of active wired markers and unique geometry. Instead of illuminating one marker at a time for unique geometry tools, the system control unit illuminates an entire face.

In some instances, if a view of the tool has been blocked from the position sensor and then comes back into a field of view of the position sensor, the position sensor has no knowledge of which face it is looking at so it systemically determines which face the position sensor is viewing. For example, if the position sensor tracks a face and the face goes missing from a field of view of the sensor, the sequencing may start from the adjacent face to determine which face is now in the field of view of the sensor. The system control unit or controller may accomplish this by activating markers sequentially until a marker is detected by the sensor.

For an illustrative tool, a smart algorithm to reduce the lock-on time and increase efficiency of the searching process may be employed. Instead of firing/activating the IREDs or LEDs by the natural order (e.g., 1, 2, 3, etc.), the system control unit can fire/activate the IREDs or LEDs by each face by firing a primary IRED or LED of each face. When the position sensor identifies the IRED or LED, it then sequences then the IREDs or LEDs on the face to identify its orientation. For example, in the conventional manner, if a tool has 16 LEDs that is divided into 8 faces (each face shares 2 LEDs with its adjacent face), to detect the last face at least 19 LEDs would need to be fired using a conventional algorithm (4 LEDs for a face and to get a transformation 3 LEDs are enough). In the suggested method using the smart algorithm, only 10 LEDs would need to be fired (8 faces plus 2 LEDs in the last face), which may produce a difference of, for example, a decrease of approximately 150 ms in the lock-on time for a 60 Hz refresh rate.

For both types of tools—a standard geometry tool and/or a unique geometry tool—instead of firing/activating the faces in an order, another approach may be used. The approach may divide the faces into two adjacent groups—a first group and a second group—and activate all of the markers in the first group. If the position sensor detects IREDs or LEDs, then the first group is divided into two sub-groups and markers of each sub-group is activated until the position sensor detects IREDs or LEDs. If the position sensor does not detect IREDs or LEDs, then the markers in the second group are activated. In such embodiments, the lock-on time may be reduced. For example, for a tool with eight faces, to detect the last face, markers on eight faces would need to be activated, i.e. 16 frames of activation. If the suggested algorithm is used, only six frames are needed to detect the faces, which may result in a difference of, for example, a decrease of approximately 166 ms in the lock-on time for a 60 Hz refresh rate.

In some embodiments, the multi-face active wired tool may be positioned on a robotic arm. This connection may provide the position sensor a prediction of which face is in the field of view of the sensor, and as a result may reduce the lock-on time significantly. This algorithm or sequence utilizes this communication such that whenever a tool goes missing, the system control unit will calculate the predicted face within the field of view of the sensor according to the solver information and illuminate only the relevant IREDs or LEDs instead of starting a standard, conventional sequencing. For example, for a standard geometry tool, having 16 LEDs that is divided into eight faces (each face shares 2 LEDs with its adjacent face), to detect the last face using a conventional algorithm, at least 19 LEDs (4 LEDs for a face and to get a transformation, 3 LEDs are enough) would need to be activated. Using the algorithm or sequence, only 3 LEDs would need to be activated, which may result in a difference of about 533 ms lock-on time for a 60 Hz refresh rate.

Embodiments of the present disclosure provide technical solutions to one or more of the problems of (1) determining a pose of a tool based on a tracking device mounted to the tool, (2) improving a lock-on time of a sensor to a tracking device, (3) tracking a tool based on a tracking device mounted to the tool, (4) validating a pose of a robotic arm during a surgical procedure, and (5) reducing an overall operating time.

Turning first to FIG. 1, a block diagram of a system 100 according to at least one embodiment of the present disclosure is shown. The system 100 may be used to determine a pose of an object (e.g., a tool, an instrument, an end effector, a robotic arm, an anatomical element of a patient, or the like) and/or carry out one or more other aspects of one or more of the methods disclosed herein. The system 100 comprises a computing device 102, one or more sensors 112, a robot 114, one or more controllers 126, one or more tracking devices 200, 300, 400, a navigation system 118, a database 130, and/or a cloud or other network 134. Systems according to other embodiments of the present disclosure may comprise more or fewer components than the system 100. For example, the system 100 may not include the robot 114, the navigation system 118, the controller 126, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the sensor 112, the robot 114, the controller 126, the tracking device 200, 300, 400, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 500, 600, 700, 800, and/or 900 described herein, or of any other methods. The memory 106 may store, for example one or more sequencing algorithms 122 and/or instruction(s) 124. Such instructions 124 or algorithms 122 may, in some embodiments, be organized into one or more applications, modules, packages, layers, neural networks, or engines. The algorithms 122 and/or instructions 124 may cause the processor 104 to manipulate data stored in the memory 106 and/or received from or via the sensor 112, the robot 114, the controller 126, the tracking device 200, 300, 400, the navigation system 118, the database 130, and/or the cloud 134.

The computing device 102 may also comprise a communication interface 108. The communication interface 108 may be used for receiving sensor data or other information from an external source (such as the sensor 112, the robot 114, the controller 126, the tracking device 200, 300, 400, the navigation system 118, the database 130, the cloud 134, and/or any other system or component not part of the system 100), and/or for transmitting instructions, images, or other information to an external system or device (e.g., another computing device 102, the sensor 112, the robot 114, the controller 126, the tracking device 200, 300, 400, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, Zig-Bee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions such as the instructions 124 to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The system 100 includes the one or more sensor(s) 112. The sensor 112 is operable to detect a plurality of markers 204 disposed on the tracking device 200, 300, 400 (described in detail with respect to FIGS. 2A-4). The sensor 112 may be, for example, an optical camera; an infrared camera; a 3D camera system; a stereoscopic vision system; an imaging device; or any other sensor that can detect the plurality of markers 204. In some examples, the markers 204 may be active markers and the sensor 112 may be configured to sense the markers 204 when the markers 204 are activated (by the controller 126, for example). In such examples, the markers 204 may be an infrared light emitting diode and the sensor 112 may be an infrared camera configured to sense when the markers 204 emit infrared light.

The sensor 112 may comprise a dedicated processor for executing instructions stored in a dedicated memory of the sensor 112, or the sensor 112 may simply be configured to transmit data collected therewith to the computing device 102 or to another component of the system 100. Although shown in FIG. 1 as being in communication only with the computing device 102, in some embodiments, the sensor 112 may be in communication with any one or more of the tracking device 200, 300, 400, the computing device 102, the robot 114, the controller 126, the navigation system 118, the database 130, and/or the cloud 134. Also, in some embodiments, the computing device 102 may comprise the sensor 112, while in other embodiments, the navigation system 118 may comprise the sensor 112. In still other embodiments, the robot 114 may comprise the sensor 112.

The sensor 112 may be positioned directly above an operating table or portion thereof, or above and to one side of an operating table or portion thereof, or in another convenient position within an operating room or other room. The sensor 112 may be positioned at a location selected to provide the sensor 112 with a clear and/or unobstructed view of the tracking device 200, 300, 400 (and thus of one or more markers 204 fixedly secured to the tracking device 200, 300, 400) during operation thereof. In some embodiments, the sensor 112 is fixed, while in other embodiments, the sensor 112 may be precisely movable (whether manually or automatically) in one or more directions.

The sensor 112 may be configured to capture data regarding sensed markers 204 only at a given moment in time. For example, where the sensor 112 is a camera, the sensor 112 may be configured to capture still images comprising one or more markers 204. The sensor 112 may be configured to capture such data at periodic intervals, or when commanded by a user (e.g., via a user interface 112), or upon a signal (generated either autonomously or in response to user input) from the controller 126, the computing device 102, the robot 114, and/or the navigation system 118.

The sensor 112 may additionally or alternatively be operable to capture data corresponding to the plurality of markers 204 continuously, in real-time. In such embodiments, the sensor 112 may provide a stream of real-time sensor data to the computing device 102, which may continuously process the sensor data to detect the markers 204 therein. In some embodiments, the sensor 112 may comprise more than one sensor 112.

Still referring to FIG. 1, the robot 114 may be any surgical robot or surgical robotic system. The robot 114 may be or comprise, for example, the Mazor X™ Stealth Edition robotic guidance system. The robot 114 may be configured to position the tracking device, 200, 300, 400, for example, at one or more precise position(s) and orientation(s), and/or to return the tracking device, 200, 300, 400 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the tracking device, 200, 300, 400. In embodiments where two tracking devices 200, 300, 400 are used, one robotic arm 116 may hold a first tracking device, and another robotic arm 116 may hold a second tracking device. Each robotic arm 116 may be positionable independently of the other robotic arm. It will be appreciated that any number of robotic arms 116 may be used to support or hold any number of tracking device 200, 300, 400. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, a tracking device 200, 300, 400, a surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) or markers 204 (shown in FIGS. 2A-4), may be placed on the robot 114 (including, e.g., on the robotic arm 116) or any other object in the surgical space. The markers 204 may be tracked by the navigation system 118, and the results of the tracking may be used by the robot 114 and/or by an operator of the system 100 or any component thereof. In some embodiments, the navigation system 118 can be used to track other components of the system and the system can operate without the use of the robot 114 (e.g., with the surgeon manually manipulating one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) such as the sensor 112 for tracking the markers 204, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (i.e., pose) of the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, sensor 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In the illustrated embodiment, the system 100 includes the controller 126, though in some embodiments the system 100 may not include the controller 126. The controller 126 may be an electronic, a mechanical, or an electro-mechanical controller. The controller 126 may comprise or may be any processor described herein. The controller 126 may comprise a memory storing instructions for executing any of the functions or methods described herein as being carried out by the controller 126. In some embodiments, the controller 126 may be configured to simply convert signals received from the computing device 102 (e.g., via a communication interface 108) into commands for operating the tracking device 200, 300, 400 (and more specifically, for activating markers 204 fixedly secured to the tracking device 200, 300, 400), the sensor 112, the navigation system 118, and/or the robot 114. In other embodiments, the controller 126 may be configured to process and/or convert signals received from the tracking device 200, 300, 400, the sensor 112, the navigation system 118, and/or the robot 114. Further, the controller 126 may receive signals from one or more sources (e.g., the tracking device 200, 300, 400, the sensor 112, the navigation system 118, and/or the robot 114) and may output signals to one or more sources.

The controller 126 is operable to cause one or more markers of a plurality of markers 204 to selectively activate. The controller 126 may cause the one or more markers to activate for any duration of time, at any intensity, and/or at any wavelength. In some embodiments, the controller 126 may cause one or more markers to selectively activate in sequence. In other embodiments, the controller 126 may cause one or more markers to activate one at a time. In still other embodiments, the controller 126 may cause one or more sets of markers to activate at the same time, while deactivating markers not in the one or more sets of markers.

The system 100 also includes a tracking device 200, 300, 400 described in detail below with respect to FIGS. 2A-4. The tracking device 200, 300, 400 may be mounted to a tool or an end effector supported by a robotic arm such as the robotic arm 116. By mounting the device 200, 300, 400 to the tool, the end effector, or any other object, a pose of such tool, end effector, or object may be determined based on a pose of the device 200, 300, 400. In some embodiments, the pose of the tracking device 200, 300, 400 may be used to determine and validate a pose of a robotic arm such as the robotic arm 116. In such embodiments, the pose of the robotic arm 116 as determined by the tracking device 200, 300, 400 may be compared to the pose of the robotic arm 116 as determined from the robotic arm 116 (using, for example, sensors disposed or integrated with the robotic arm 116) to validate the pose of the robotic arm 116.

Figure 2A:
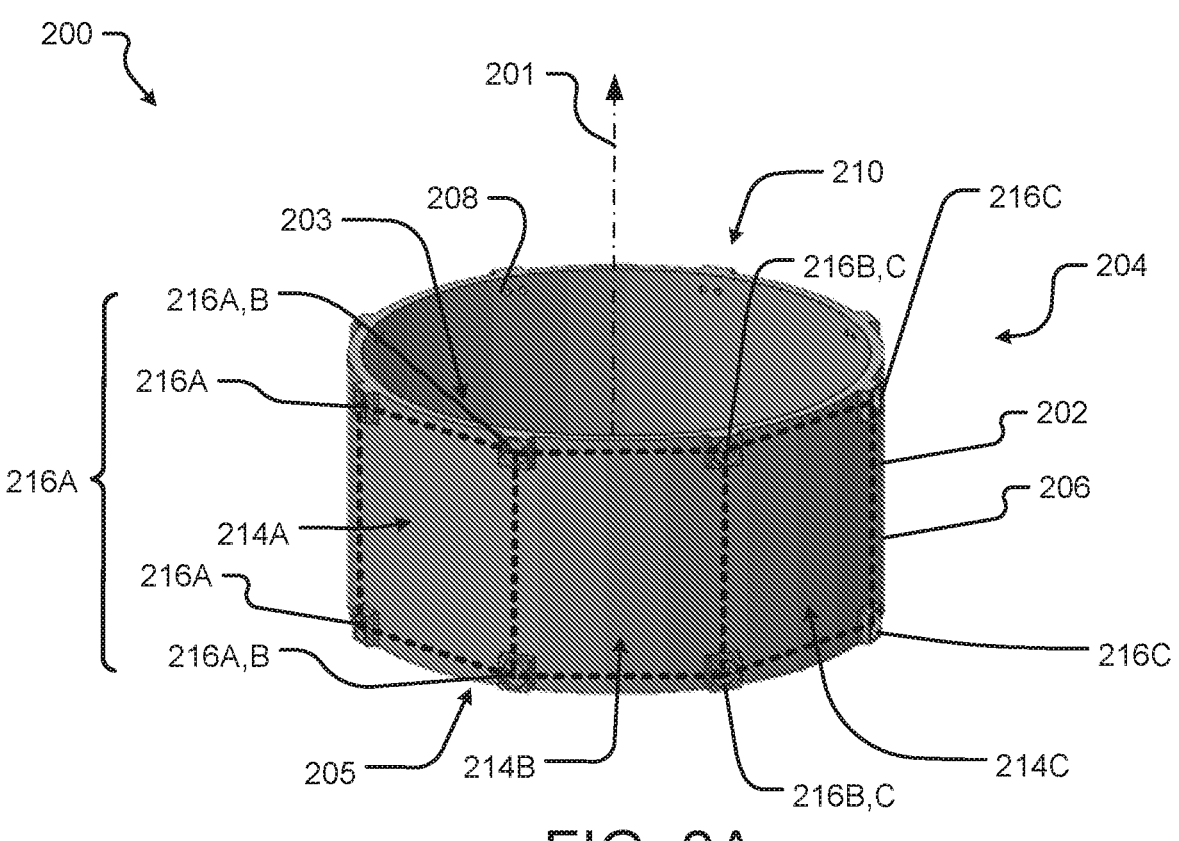
FIG. 2A is an isometric view of a tracking device according to at least one embodiment of the present disclosure.

Turning to FIG. 2A, a tracking device 200 is shown. The tracking device 200 includes a body 202. The body 202 may be formed from any material such as, for example, ceramic, aluminum, steel, or the like. In the illustrated embodiment, the body 202 a cross-section of the body 202 is cylindrical. In other embodiments, the cross-section of the body 202 may be any shape such as a square, an oval, a rectangle, or the like. In some embodiments the body 202 has a height of about 70 mm. In other embodiments, the body may have a height less or greater than 70 mm. In some embodiments, the body has a diameter of about 5.5 mm. In other embodiments, the body may have a diameter less or greater than 5.5 mm.

The body 202 includes an outer surface 206, an inner surface 208, and an interior space 210. The outer surface 206 may be smooth, as illustrated, or may have any texture. The outer surface 206 may also be curved, as shown, or may have any shape or form. A plurality of faces or segments 214 may span across the outer surface 206 and extend around a circumference of the body 202. In some embodiments, the plurality of faces 214 may include eight adjacent faces. In such embodiments, each face is adjacent to two other faces. In other embodiments, the plurality of faces 214 may include fewer or more than eight faces. In yet other embodiments, some faces may be adjacent to one, two, or more than two faces, and/or some faces may not be adjacent to any faces. A boundary of four faces of the plurality of faces 214 is shown in dotted lines in FIG. 2A for illustrative purposes. In some embodiments, each face may have a length of about 40 mm. In other embodiments, each face may have a length less or greater than 40 mm.

In the illustrated embodiment, a plurality of markers 204 are fixedly secured to the outer surface 206. The plurality of markers 204 are distributed around a circumference of the body 202 and provide 360 degrees of markers on the device 200 so that at least one marker 204 is visible or in a field of view of a sensor such as the sensor 112 at any rotational position of the device 200. In some embodiments, the plurality of markers 204 include 16 markers. In other embodiments, the plurality of markers 204 include fewer or more than 16 markers.

The plurality of markers 204 may be spaced so that at least one marker may be visible in a field of view of a sensor such as the sensor 112 at any given position, so long as a line of sight between the device 200 and the sensor 112 is clear or not blocked. As shown, the plurality of markers 204 may include a first row of markers 203 and a second row of markers 205. Each marker in the first row 203 and the second row 205 may be spaced equidistance and symmetrically around the body 202, though as will be shown and described below, each marker may be spaced at different distances and/or non-symmetrically from each other. In some embodiments, a marker in the first row 203 and the second row 205 may be spaced about 45 degrees from an adjacent marker in the same row and relative to a center axis 201 of the body 202. For example, marker 216A,B may be spaced about 45 degrees from marker 216B,C. In other embodiments, a marker may be spaced less or greater than 45 degrees from an adjacent marker.

The plurality of markers 204 may be active markers. In some embodiments, the plurality of markers 204 are infrared light emitting diodes. In other embodiments, the plurality of markers 204 may be any type of active markers. For example, the plurality of markers 204 may emit light in any wavelength. In some embodiments, the plurality of markers 204 may comprise different types of active markers. In other embodiments, the plurality of markers 204 may comprise the same type of active markers. In other embodiments, the plurality of markers 204 may be passive markers. For example, the plurality of markers 204 may be reflective spheres.

The plurality of markers 204 define a plurality of sets of markers 216 and each set of markers 216 is disposed on a corresponding face of the plurality of faces 214. For example, in the illustrated embodiments the set of markers 216A and 216A,B correspond to face 214A. As shown, each set of markers 216 includes four markers. In other embodiments, each set of markers 216 includes three markers. In still other embodiments, each set of markers 216 may include fewer or more than four markers. Each set of markers 216 may include the same number of markers. In other embodiments, a set of markers 216 may include a different number of markers than another set of markers 216. In the illustrated embodiment, each set of markers 216 is arranged in a square. In other embodiments, each set of markers 216 may be arranged in any shape or pattern. In still other embodiments, a set of markers 216 may be arranged in a different shape or pattern than another set of markers 216. For example, a first set of markers can be arranged in a first pattern or unique geometry and a second set of markers can be arranged in a second pattern or unique geometry different from the first pattern. Such patterns or unique geometries may aid in determining a position of the device 200 (and thus, for example, the corresponding robotic arm 116) based on the corresponding face of the pattern detectable by the sensor 112.

In the illustrated embodiment, each face 214 is defined by the corresponding set of markers 216 and adjacent faces 214 may share two markers 216. In other words, a first set of markers and a second set of markers may share two markers, while each of the first set and the second set include four markers total. For example, as shown, face 214A includes the set of markers 216A and 216A,B and face 214B includes the set of markers 216A,B and 216B,C. In other embodiments, each face 214 (and thus, the corresponding set of markers) may not share any markers with an adjacent face (and thus, the adjacent set of markers).

Figure 2B:
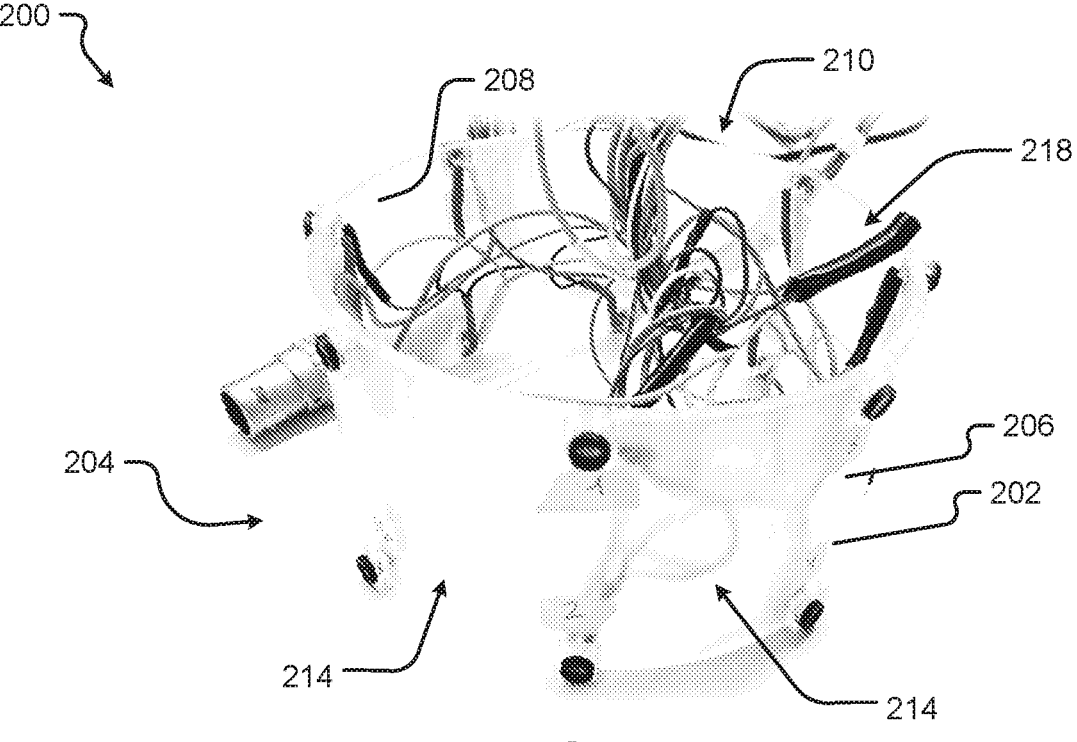
FIG. 2B is an isometric view of a tracking device according to at least one embodiment of the present disclosure.

Turning to FIG. 2B, the tracking device 200 is shown. A plurality of wires 218 may be stored in the interior space 210 of the body 202 and one or more wires of the plurality of wires 218 may be secured to the inner surface 208 of the body 202. It will be appreciated that any hardware may be stored or secured in the interior space 210. Each wire 218 may provide or deliver power to a corresponding marker 204 to selectively activate the corresponding marker 204 when power is delivered to the corresponding marker 204. In embodiments where the marker 204 is an infrared emitting light diode, activating the marker 204 causes the marker 204 to emit infrared light. Conversely, the marker 204 does not emit infrared light when power is not delivered to the marker 204 and the marker 204 is not activated.

Though not illustrated, the tracking device 200 may be mounted to, installed on, or otherwise secured to any object such as an end effector, a robotic arm (including, for example, an end of the robotic arm, a joint of the robotic arm, a segment of the robotic arm, or any portion of the robotic arm), or any other component.

Figure 3:
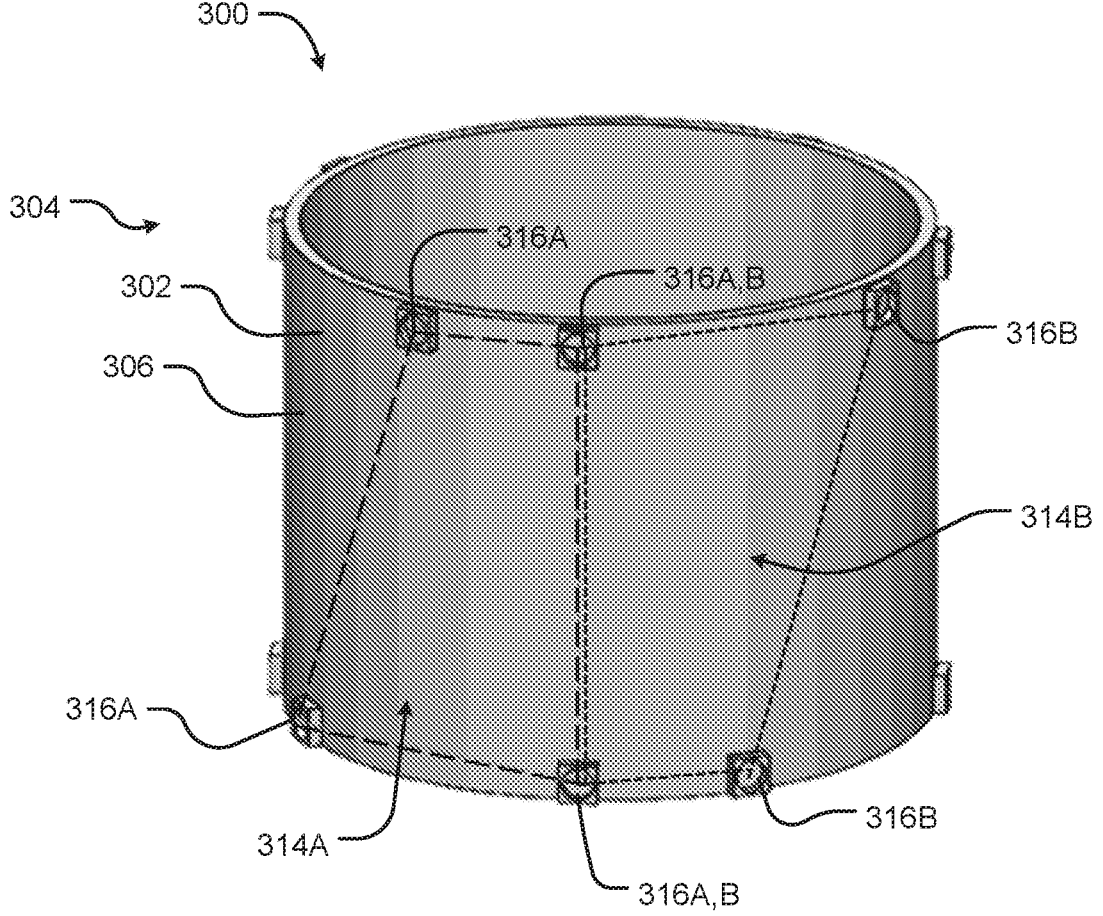
FIG. 3 is an isometric view of a tracking device according to at least one embodiment of the present disclosure.

Turning to FIG. 3, a tracking device 300 according to at least one embodiment is shown. The tracking device 300 may be the same as or similar to the tracking device 200 described above. In the illustrated embodiment, a plurality of markers 304 are fixedly secured to an outer surface 306 of a body 302. The plurality of markers 304 define a plurality of sets of markers 316 and each set of markers 316 is disposed on a corresponding face of the plurality of faces 314. As shown, each set of markers 316 includes four markers. In other embodiments, each set of markers 316 may include fewer or more than four markers. In still other embodiments, a set of markers 316 may include a different number of markers than another set of markers 316.

In the illustrated embodiment, each set of markers 316 defines a trapezoid, shown in broken lines for illustrative purposes. In some embodiments, a first segment of the trapezoid may be about 27 mm, a second segment of the trapezoid may be about 68 mm, a third segment of the trapezoid may be about 51 mm, and a fourth segment of the trapezoid may be about 73 mm. In other embodiments, the first segment may be less or greater than 27 mm, the second segment may be less or greater than 68 mm, the third segment may be less or greater than 51 mm, and the fourth segment may be less or greater than 73 mm. Also shown in the illustrated embodiment, a first set of markers 316A and 316A,B corresponding to a face 314A is rotated 180 degrees from an adjacent and second set of markers 316B and 316A,B corresponding to a face 314B. In other words, the set of markers 316 may be an inverse pattern of a pattern of the adjacent set of markers 316 (and as illustrated, for example, an inverse trapezoid of the adjacent trapezoid). In other embodiments, each set of markers 316 may be configured in any shape or pattern. In yet other embodiments, a set of markers 316 may be configured in a different shape or pattern than another set of markers 316. In the illustrated embodiment, each face 314 is defined by the corresponding set of markers 316 and adjacent faces 314 may share two markers 316. In other words, a first set of markers and a second set of markers may share two markers, while each of the first set and the second set include four markers total. In other embodiments, each face 314 (and thus, the corresponding set of markers) may not share any markers with an adjacent face (and thus, the adjacent set of markers).

Figure 4:
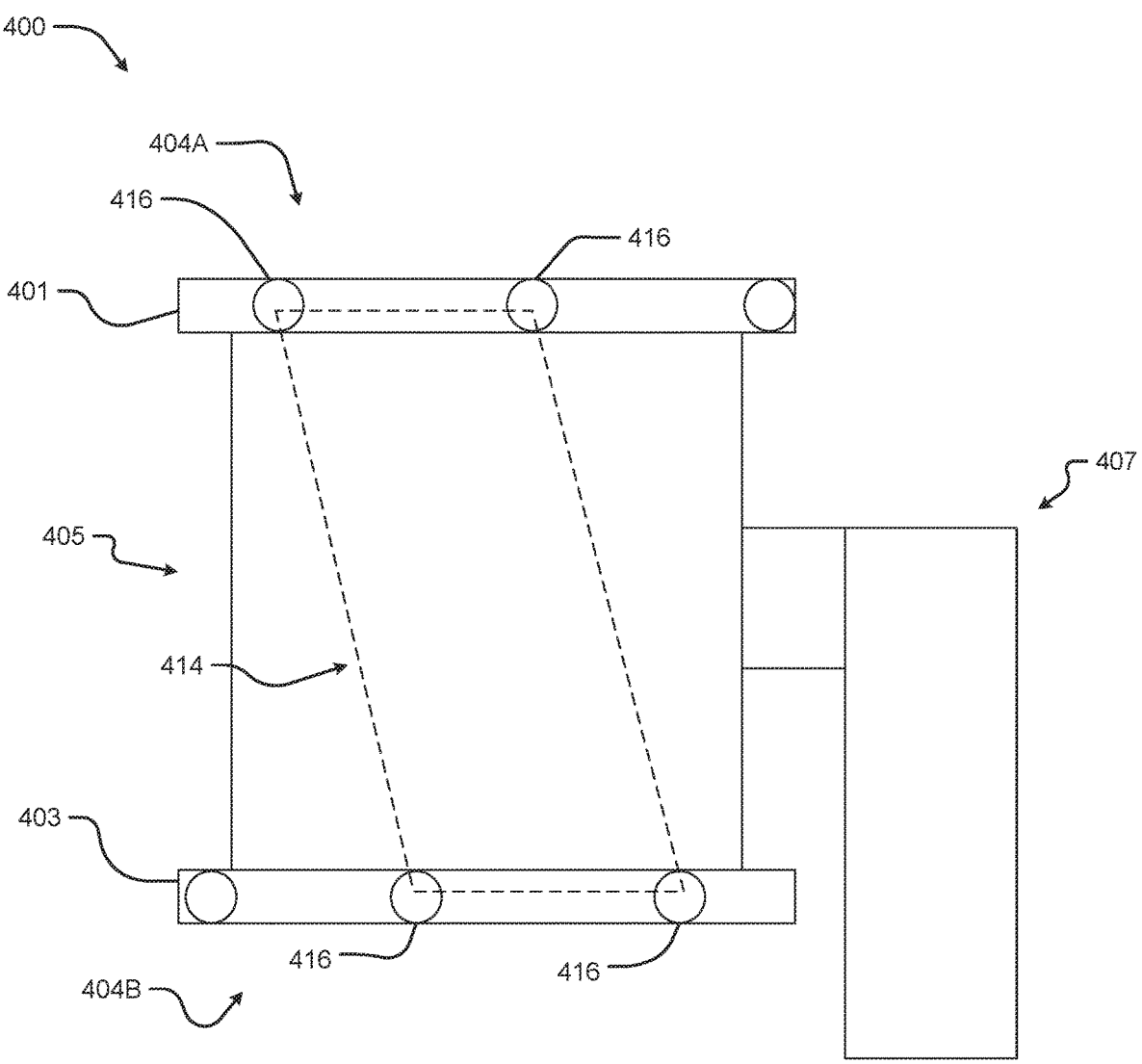
FIG. 4 is an isometric view of a tracking device according to at least one embodiment of the present disclosure.

Turning to FIG. 4, a tracking device 400 according to at least one embodiment is shown. The tracking device 400 may be the same as or similar to the tracking device 200 described above except for the tracking device 400 includes a first ring 401 spaced from a second ring 403. In some embodiments, the first ring 401 is spaced from the second ring 403 a distance of about 68.5 mm. In other embodiments the first ring 401 may be spaced from the second ring 403 a distance of less or greater than 68.5 mm. Though the first ring 401 and the second ring 403 are shown having a cross-section that is circular, it will be appreciated that the first ring 401 and the second ring 403 may have any cross-section with any shape such as, for example, a rectangle, a square, or an oval. The device 400 also includes a base 405 spanning a distance between the first ring 401 and the second ring 403. The base 405 may support, for example, hardware, wires, a connector 407 (for connecting the device 400 to an end effector or robotic arm, for example), or the like.

A first plurality of markers 404A is disposed on the first ring 401 and a second plurality of markers 404B is disposed on the second ring 403. The first plurality of markers 404A and the second plurality of markers 404B define a plurality of sets of markers 416, wherein each set of markers 416 comprises one or more markers of each of the first plurality of markers 404A and the second plurality of markers 404B. Each set of markers 416 may belong to or define a corresponding face of a plurality of faces 414. In the illustrated embodiment, one face 414 is shown in dotted lines for illustrative purposes.

In some embodiments the first plurality of markers 404A includes the same number of markers as the second plurality of markers 404B. In other embodiments, the first plurality of markers 404A may have more or fewer markers than the second plurality of markers 404B. Similarly, in some embodiments, the first plurality of markers 404A may be disposed on the first ring 401 in the same arrangement as the second plurality of markers 404B is disposed on the second ring 403. In other embodiments, the first plurality of markers 404A may be disposed on the first ring 401 in a different arrangement as the second plurality of markers 404B disposed on the second ring 403. In the illustrated embodiment—where the first ring 401 and the second ring 403 are identical (in other words, the first plurality of markers 404A and the second plurality of markers 404B are disposed in the same arrangement on the first ring 401 and the second ring 403, respectively)—the first ring 401 and the second ring 403 are aligned so as to offset the first plurality of markers 404A and the second plurality of markers 404B. In such embodiments, each face of the plurality of faces may be shaped as, for example, a parallelogram. In other embodiments, the first ring 401 and the second ring 403 may be aligned so as to align the first plurality of markers 404A and the second plurality of markers 404B. In such embodiments, each face of the plurality of faces may be shaped as, for example, a rectangle, or, depending on the spacing between the first ring 401 and the second ring 403, a square. It will be appreciated that the first plurality of markers 404A and the second plurality of markers 404B may be disposed in any arrangement to define each face of the plurality of faces in any shape.

Though the device 200, 300 includes a body 202, 302 with respect to FIGS. 2A, 2B, and 3 and the device 400 includes a first ring 401, a second ring 403, and a base 405, it will be appreciated that any embodiment can include any combination of or any number of a body, a base, and a ring. For example, the device 300 may include a first ring and a second ring instead of a body. In another example, the device 400 may include a body instead of a first ring and a second ring.

The system 100 or similar systems of FIG. 1 and the tracking device 200, 300, 400 or similar tracking devices of FIGS. 2A-4 may be used, for example, to carry out one or more aspects of any of the methods 500, 600, 700, 800 and/or 900 described herein. The system 100 or similar systems and/or the tracking device 200, 300, 400 or other similar tracking devices may also be used for other purposes.

FIG. 5 depicts a method 500 that may be used, for example, for determining a tool pose.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions such as instructions 124 stored in a memory such as the memory 106. The instructions may correspond to one or more steps of the method 500 described below. The instructions may cause the processor to execute one or more algorithms, such as a sequencing algorithm 122.

The method 500 comprises causing a controller to activate one marker from a set of markers (step 504). The controller may be the same as or similar to the controller 126 and the set of markers may be the same as or similar to the set of markers 216, 316, 416. The set of markers may be part of a plurality of sets of markers. Each set of markers may comprise one or more markers of a plurality of markers (such as the plurality of markers 204, 304, 404A, 404B) fixedly secured to a tracking device such as the tracking device 200, 300, 400. Each set of markers may define a corresponding face of a plurality of faces such as the plurality of faces 214, 314, 414.

The tracking device may be mounted to a tool. In some embodiments, the tool is supported by a robotic arm such as the robotic arm 116. In other embodiments, the tool is an end effector supported by a robotic arm. During use, a pose of the tracking device may be determined as described herein. By determining a pose of the tracking device, a pose of the tool can also be determined relative to the pose of the tracking device.

In some embodiments where each of the plurality of markers is an infrared light emitting diode, activating a marker causes the marker to emit infrared light. The infrared light may be detected by a sensor such as the sensor 112, which may be, for example, an infrared camera. In other embodiments, activating the marker may cause the marker to emit a light of any wavelength. Activating the marker may include using, for example, a processor such as the processor 104 to generate instructions such as the instructions 124 and transmitting the instructions to the controller. Further, the controller may activate one or more markers in sequence using an algorithm such as the sequencing algorithm 122. In some embodiments, the controller activates one marker from each set of markers, in sequence until an activated marker is detected by the sensor. By activating one marker at a time, a face corresponding to the activated marker can be determined, as described below.

The method 500 also comprises receiving information about a detected activated marker (step 508). The information may be received from the sensor configured to detect an activated marker. The sensor may be a camera such as, for example, an infrared camera or an optical camera. The information may include, for example, a detected position of the detected activated marker.

The method 500 also comprises causing the controller to activate the set of markers comprising the detected activated marker (step 512). The step 512 may be the same as or similar to the step 504 described above with respect to activating one or more markers. In some embodiments, each marker of the set of markers may be activated in sequence. In other embodiments, the entire set of markers may be activated at the same time. The detected activated marker corresponds to a face of the plurality of faces and thus, the set of markers comprising the activated marker corresponds to the face as well. By activating the set of markers corresponding to the face, an orientation of the face may be determined, as described below.

The method 500 also comprises receiving information about the activated set of markers (step 516). The information may be received from the sensor, which may be a camera such as, for example, an infrared camera or an optical camera. The information may include a detected position of each marker of the activated set of markers. The information may also include a pattern or arrangement of the activated set of markers.

In some embodiments, the information about the activated set of markers is information about the activated set of markers activated in step 512. In other embodiments, the information about the activated set of markers may be obtained from other methods or steps described herein. In other words, the steps 520 and 524 below describing determining a pose of the tool may be applied to information about an activated set of markers obtained using methods other than the steps 504-512 described above. For example, the information may be received from the steps 804-812, for example.

The method 500 also comprises determining a face of a plurality of faces having the at least one set of markers (step 520). The face may be determined based on the detected position of each marker of the activated set of markers. Further, an orientation of the face may be determined based on the detected position of each marker of the activated set of markers. In embodiments where a corresponding set of markers is arranged in a unique pattern on each face, the face may also be determined based on the pattern of the activated set of markers.

The method 500 also comprises determining a pose of the tool and/or the robotic arm based on the information and the determined face (step 524). More specifically, the pose of the tool and/or the robotic arm may be based on the determined face and the orientation of the determined face.

The method 500 also comprises validating a pose of the tool and/or robotic arm based on the determined pose of the tool and/or robotic arm (step 528). The pose of the tool and/or the robotic arm may be validated by comparing the determined pose of the tool and/or robotic arm as determined in, for example, step 524 to pose information received from the robotic arm. In some embodiments, the robotic arm may include one or more sensors configured to sense a pose of the robotic arm and yield pose information. When the pose information received from the robotic arm matches the determined pose determined from the tracking device, then this indicates that the pose of the tool and/or robotic arm is validated. When the pose information received from the robotic arm does not match the determined pose determined from the tracking device, then this indicates that an error has occurred. The error may be related to, for example, a navigation system such as the navigation system 118 and/or a registration process.

The present disclosure encompasses embodiments of the method 500 that comprise more or fewer steps than those described above, and/or one or more steps that are different than the steps described above.

Figure 6:
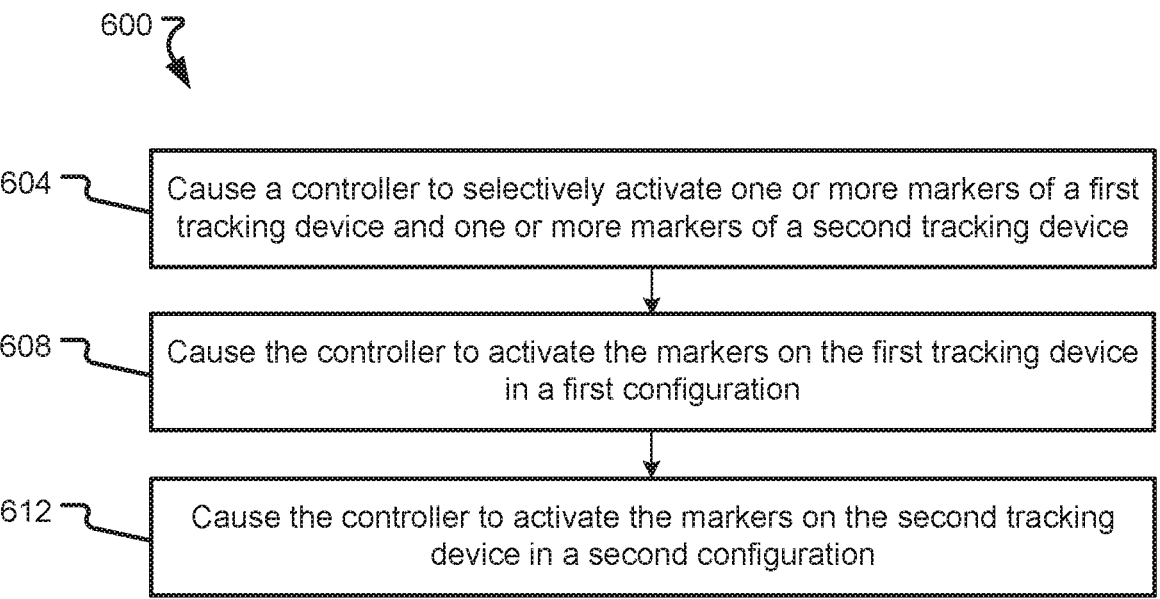
FIG. 6 is a flowchart according to at least one embodiment of the present disclosure.

FIG. 6 depicts a method 600 that may be used, for example, for tracking multiple objects.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing instructions such as the instructions 124 stored in a memory such as the memory 106. The instructions may correspond to one or more steps of the method 600 described below. The instructions may cause the processor to execute one or more algorithms, such as a sequencing algorithm 122.

The method 600 comprises causing a controller to selectively activate one or more markers of a first tracking device and one or more markers of a second tracking device (step 604). The step 614 may be the same as or similar to the step 504 of method 500 with respect to activating one or more markers. Each of the first tracking device and the second tracking device may be the same as or similar to the tracking device 200, 300, 400. In some embodiments, the first tracking device is identical to the second tracking device. In other embodiments, the first tracking device may be different from the second tracking device. The controller may be the same as or similar to the controller 126. In some embodiments, one controller may control each of the first tracking device and the second tracking device. In other embodiments, a first controller may control the first tracking device and a second controller may control the second tracking device.

The one or more markers of the first tracking device may be releasably or fixedly secured to the first tracking device in a first arrangement and the one or more markers of the second tracking device may be fixedly secured to the second tracking device in a second arrangement. In some embodiments, the first arrangement is the same as the second arrangement. In other embodiments, the first arrangement may be different from the second arrangement.

The method 600 also comprises causing the controller to activate the markers on the first tracking device in a first configuration (step 608). In some embodiments, the first configuration may be a first sequence and the controller may use an algorithm such as the sequencing algorithm 122 to cause the markers on the first tracking device to activate in the first sequence. For example, each marker of the one or more markers on the first tracking device may be activated one at a time in sequence, two or more markers may be activated together in sequence, or two or more markers may be activated together in a pattern. In other embodiments, the first configuration may be a first wavelength. The wavelength may include, for example, infrared light, visible light, or ultraviolet light. In some embodiments, the wavelength may be between about 700 nm to 1 mm. In other embodiments, the wavelength may be about 880 nm. In still other embodiments, the wavelength may be less than 700 nm or greater than 1 mm. In still other embodiments, the wavelength may be any wavelength within the infrared spectrum. In some embodiments, the first configuration may include a combination of sequences and/or wavelengths.

The method 600 also comprises causing the controller to activate the markers on the second tracking device in a second configuration (step 612). In some embodiments, the second configuration may be a second sequence and the controller may use an algorithm such as the sequencing algorithm 122 to cause the markers on the second tracking device to activate in the second sequence. The second sequence may be the same as or similar to the first sequence. In such instances, the second sequence may be activated before or after the first sequence to distinguish the second tracking device from the first tracking device. In other instances, the second sequence may be different from the first sequence. In such instances, the second sequence may be unique to the second tracking device so as to distinguish the second tracking device from the first tracking device. In other embodiments, the second configuration may be a second wavelength. The second wavelength may be the same as or similar to the first wavelength. In other instances, the second wavelength may be different from the first wavelength. In still other embodiments, the first configuration may include a combination of sequences and/or wavelengths.

In other examples, a pose of the first tracking device and the second tracking device may be determined from, for example, a first robotic arm and a second robotic arm that the first tracking device and the second tracking device are mounted to, respectively. As such, the second tracking device can be distinguished from the first tracking device based on a known pose of the first robotic arm and the second robotic arm. In such examples, the markers on each of the first tracking device and the second tracking device may be used to confirm an orientation of the first tracking device and the second tracking device.

The present disclosure encompasses embodiments of the method 600 that comprise more or fewer steps than those described above, and/or one or more steps that are different than the steps described above.

Turning to FIGS. 7-9, methods 700, 800, 900 relate to determining a tool or object pose based on sequencing one or more markers on a tracking device to which the tool or object is coupled or mounted thereon. The methods 700, 800, 900 may be used, for example, in instances where a tracking device such as the tracking device 200, 300, 400 exits a field of view of a sensor such as the sensor 112 and re-enters the field of view. In such instances, the sensor 112 no longer has information describing which face of a plurality of faces of the tracking device is within the field of view. By sequencing the one or more markers in the methods 700, 800, 900 described below, a lock-on time of a sensor to the face of the tracking device may be reduced. Such reduction in lock-on time may reduce an overall time of a surgical procedure.

FIG. 7 depicts a method 700 that may be used, for example, for determining a tool pose.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing instructions such as the instructions 124 stored in a memory such as the memory 106. The instructions may correspond to one or more steps of the method 700 described below. The instructions may cause the processor to execute one or more algorithms, such as a sequencing algorithm 122.

The method 700 comprises determining a predicted segment (or face) of a plurality of segments of a tracking device within a field of view of a sensor (step 704). The tracking device may be the same as or similar to the tracking device 200, 300, 400, the plurality of segments may be the same as or similar to the plurality of segments 214, 314, 414, and the sensor may be the same as or similar to the sensor 112. The tracking device may be supported by a robotic arm such as the robotic arm 116. In some embodiments, the tracking device is mounted to, for example, an object or a tool supported by the robotic arm. Determining the predicted segment may be based on a known pose of the robotic arm and in some instances, a known pose of the sensor. More specifically, a field of view can be determined based on a known pose of the sensor and the predicted segment within the field of view can be determined based on the known pose of the robotic arm within the field of view.

The method 700 also comprises causing a controller to activate one or more markers of a plurality of markers on a tracking device (step 708). The tracking device may be the same as or similar to the tracking device 200, 300, 400 and the plurality of markers may be the same as or similar to the plurality of markers, 204, 304, 404A, 404B. The step 708 may be the same as or similar to the step 504 of method 500 with respect to activating one or more markers. The step 708 further includes activating one or more markers on the predicted segment identified in step 704 described above.

The method 700 also comprises identifying at least one marker of the one or more activated markers (step 712). The identified at least one marker may be identified by the sensor, for example. Identifying the at least one marker may include identifying a position of the at least one marker.

The method 700 also comprises determining an actual segment based on the identified at least one marker (step 716). The actual segment may be determined based the position of the at least one marker and may be based on a position of the tracking device. The actual segment corresponds to the segment in the field of view of the sensor.

The method 700 also comprises comparing the actual segment to the predicted segment (step 720). In embodiments where the actual segment matches the predicted segment, such a match confirms that the predicted segment is in the field of view of the sensor and the sensor may then lock onto and track the tracking device. In other embodiments, where the actual segment does not match the predicted segment, the steps 704-720 may be repeated until the actual segment matches the predicted segments. In further embodiments, where the actual segment does not match the predicted segment, another method such as method 800 and/or 900 may be utilized to determine the pose of the tool or object.

Such method 700 may reduce a lock-on time of the sensor to the tracking device. For example, if the tracking device is no longer being tracked because the tracking device was no longer in a field of view of the sensor, then re-enters the field of view of the sensor, the method 700 may be utilized to determine a predicted segment within a field of view of the sensor and confirm that the predicted segment is in fact within the field of view of the sensor. Thus, the tracking device can be identified and tracked again.

The present disclosure encompasses embodiments of the method 700 that comprise more or fewer steps than those described above, and/or one or more steps that are different than the steps described above.

FIG. 8 depicts a method 800 that may be used, for example, for determining a tool pose.

The method 800 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 800. The at least one processor may perform the method 800 by executing instructions such as the instructions 124 stored in a memory such as the memory 106. The instructions may correspond to one or more steps of the method 800 described below. The instructions may cause the processor to execute one or more algorithms, such as a sequencing algorithm 122.

The method 800 comprises causing a controller to activate one or more markers of a plurality of markers on a tracking device (step 804). The tracking device may be the same as or similar to the tracking device 200, 300, 400 and the plurality of markers may be the same as or similar to the plurality of markers, 204, 304, 404A, 404B. The step 804 may be the same as or similar to the step 504 of method 500 with respect to activating one or more markers. The step 804 further includes activating a single marker on each segment of a plurality of segments such as the plurality of segments 214, 314, 414 in sequence. By activating a single marker on each segment (until, for example, a marker is detected as described in step 808 below), a face corresponding to a detected single marker can be identified without activating each marker of the plurality of markers in sequence.

The method 800 also comprises receiving an indication from the sensor that an activated marker has been detected (step 808). The step 808 may be the same as or similar to the step 712 of step 700 with respect to identifying or detecting an activated marker.

The method 800 also comprises causing the controller to activate any remaining markers on the same segment as the activated marker (step 812). The step 812 may be the same as or similar to the step 504 of method 500 with respect to activating one or more markers. In some embodiments, the markers may be activated in sequence. In other embodiments, the markers may be activated at the same time. In yet other embodiments, some markers may be activated at the same time and other markers may be activated in sequence.

The method 800 also comprises determining an orientation of a tool based on the data from the sensor corresponding to the one or more markers (step 816). The remaining markers may be activated in step 812 to determine an orientation of the segment and thus, an orientation of the tool. More specifically, the data received from the sensor may be a position of each marker. The position of each marker may then be used to determine the orientation of the segment, and thus, based on the segment and the orientation of the segment, the orientation of the tool may be determined.

The present disclosure encompasses embodiments of the method 800 that comprise more or fewer steps than those described above, and/or one or more steps that are different than the steps described above.

FIG. 9 depicts a method 900 that may be used, for example, for determining a tool pose.

The method 900 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 900. The at least one processor may perform the method 900 by executing instructions such as the instructions 124 stored in a memory such as the memory 106. The instructions may correspond to one or more steps of the method 900 described below. The instructions may cause the processor to execute one or more algorithms, such as a sequencing algorithm 122.

The method 900 comprises causing a controller to activate all markers on a first set of segments of a plurality of segments (step 904). The controller may be the same as or similar to the controller 126. The plurality of segments may be the same as or similar to the plurality of segments 214, 314, 414. The step 904 may be the same as or similar to the step 504 of method 500 with respect to activating one or more markers. When the markers on the first set of segments are activated, the markers on the second set of segments may not be activated.

The first set of segments and a second set of segments may comprise all segments of the plurality of segments. In some embodiments each of the first set of segments and the second set of segments includes half of the segments of the plurality of segments. In other embodiments, the first set of segments may include more or fewer segments than the second set of segments.

The method 900 also comprises determining whether an activated marker has been detected (step 908). Determining whether the activated marker has been detected may be based on data received from a sensor such as the sensor 112. The sensor 112 may also determine a position of the detected activated marker.

The method 900 also comprises causing the controller to activate a first subset of markers on the first set of segments (step 912). The step 912 may be the same as or similar to the step 504 of method 500 described above with respect to activating one or more markers.

The first subset of markers on the first set of segments may be activated when an activated marker has been detected in step 908, which indicates that markers on the first set of segments is within a field of view of the sensor. In such instances, markers on the first set of segments may be divided into the first subset and a second subset. By further dividing the markers, a face of a plurality of faces of the tool may be identified by honing in on markers in a field of view of the sensor. When the first subset of markers is activated, all other markers may not be activated (such as the second subset of markers and the markers of the second set of segments).

The method 900 also comprises causing the controller to activate a second subset of markers on the first set of segments (step 916). The step 916 may be the same as or similar to the step 504 of method 500 described above with respect to activating one or more markers.

The second subset of markers on the first set of segments may be activated when an activated marker is not detected in the first subset of markers activated in step 908. When the second subset of markers on the first set of segments is activated, all other markers may not be activated (such as the first subset of markers and the markers of the second set of segments).

The method 900 also comprises causing the controller to activate all markers on a second set of segments of the plurality of segments (step 920). The step 920 may be the same as or similar to the step 504 of method 500 described above with respect to activating one or more markers.

The markers on the second set of segments may be activated when an activated marker has not been detected in step 908. In other words, when an activated marker is not detected, this may indicate that a portion of the tracking device corresponding to the first set of segments is not in the line of sight or field of view of the sensor. Thus, a portion of the tracking device corresponding to the second set of segments may be in the light of sight or field of view of the sensor. When the markers on the second set of segments is activated, the markers on the first set of segments may not be activated.

The method 900 also comprises causing the controller to activate a first subset of markers on the second set of segments (step 924). The step 924 may be the same as or similar to the step 504 of method 500 described above with respect to activating one or more markers.

The first subset of markers on the second set of segments may be activated when an activated marker has been detected in step 920. When the first subset of markers on the second set of segments is activated, all other markers may not be activated (such as a second subset of markers and the markers of the first set of segments).

The method 900 also comprises causing the controller to activate a second subset of markers on the second set of segments (step 928). The step 928 may be the same as or similar to the step 504 of method 500 described above with respect to activating one or more markers.

The second subset of markers on the second set of segments may be activated when an activated marker is not detected in the first subset of markers activated in step 924. When the second subset of markers on the second set of segments is activated, all other markers may not be activated (such as the first subset of markers and the markers of the first set of segments).

It will be appreciated that the steps 912-916 and/or the steps 924-928 may be repeated with smaller subsets until an individual segment of the plurality of segments is identified.

The present disclosure encompasses embodiments of the method 900 that comprise more or fewer steps than those described above, and/or one or more steps that are different than the steps described above.

It will be appreciated that when no active markers are detected by a sensor using any of the methods 500, 600, 700, 800, 900 described above, that a line of sight to the sensor may be obstructed. In such instances, a notification may prompt a user (such as a surgeon or other medical provider) to check that the line of sight is unobstructed and clear.

As noted above, the present disclosure encompasses methods with fewer than all of the steps identified in FIGS. 5, 6, 7, 8 and 9 (and the corresponding description of the methods 500, 600, 700, 800, and 900), as well as methods that include additional steps beyond those identified in FIGS. 5, 6, 7, 8, and 9 (and the corresponding description of the methods 500, 600, 700, 800, and 900). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for determining a tool pose, the system comprising:
    a tracking device mounted to a tool and comprising:
        a plurality of faces; and
        a set of emissive markers disposed on each face of the plurality of faces;
    at least one processor; and
    a memory storing data for processing by the at least one processor that, when processed, causes the at least one processor to:
        sequentially activate only one marker on each face of the tracking device;
        identify which of the activated markers is detected by an imaging device;
        determine which face of the plurality of faces has the identified marker disposed thereon;
        activate the set of emissive markers on the determined face; and
        determine a pose of the tool based on information about the activated set of markers.

2. The system of claim 1, wherein the information includes a detected position of each marker of the activated set of markers.

3. The system of claim 1, wherein a first face and a second face adjacent to the first face share at least two markers.

4. The system of claim 1, wherein a first set of markers is arranged in a different pattern than a second set of markers.

5. The system of claim 1, wherein the information is received from the imaging device.

6. The system of claim 1, wherein the tool is supported by a robotic arm.

7. The system of claim 1, wherein the imaging device comprises:
    a sensor configured to detect the activated set of markers, and wherein the information about the activated set of markers is received from the sensor.

8. The system of claim 1, wherein the plurality of faces extend around a circumference of the tool.

9. The system of claim 1, wherein each face of the plurality of faces includes at least three markers.

10. The system of claim 1, wherein the plurality of faces includes eight adjacent faces, each face adjacent to two other faces.

11. The system of claim 1, wherein a first set of markers of the set of emissive markers is disposed in a first pattern and a second set of markers of the set of emissive markers is disposed in a second pattern.

12. The system of claim 11, wherein the second pattern is an inverse pattern of the first pattern.

13. The system of claim 11, wherein the first pattern and the second pattern are each a trapezoid.

14. The system of claim 11, wherein the first pattern and the second pattern are identical.

* * * * *